United States Patent [19]
Djuric et al.

[11] Patent Number: 5,135,941
[45] Date of Patent: Aug. 4, 1992

[54] LTB₄ SYNTHESIS INHIBITORS

[75] Inventors: Stevan W. Djuric, Glenview; Richard A. Haack; Julie M. Miyashiro, both of Chicago, all of Ill.

[73] Assignee: G. D. Searle & Co., Chicago, Ill.

[21] Appl. No.: 787,274

[22] Filed: Nov. 4, 1991

Related U.S. Application Data

[62] Division of Ser. No. 452,138, Dec. 18, 1989, Pat. No. 5,086,067.

[51] Int. Cl.⁵ .................... A61K 31/41; A61K 31/18; C07C 303/00; C07D 257/00
[52] U.S. Cl. ...................... 514/381; 564/91; 514/602; 548/252; 548/253
[58] Field of Search .................. 564/91; 514/602, 381; 548/252, 253

[56] References Cited
U.S. PATENT DOCUMENTS
3,917,692  11/1975  Grunwald .......................... 564/91

*Primary Examiner*—Patricia L. Morris
*Assistant Examiner*—Robert C. Whittenbaugh
*Attorney, Agent, or Firm*—Roger A. Williams; Paul D. Matukaitis

[57] ABSTRACT

This invention relates to a compound of the formula:

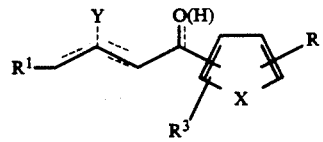

or a pharmaceutically acceptable salt thereof wherein X is oxygen, sulfur, —CH=CH— or —CH=N—; wherein $R_1$ is alkyl, alkenyl or alkynyl of about 1 to 20 carbon atoms; wherein R is —$CO_2R^2$, tetrazole, methylsulfonamide or benzenesulfonamide, wherein $R^2$ is hydrogen, alkyl of 1 to 6 carbon atoms or a pharmaceutically acceptable cation and $R^3$ is hydroxyl or halogen, having utility as LTB₄ synthesis inhibitors.

7 Claims, No Drawings

LTB4 SYNTHESIS INHIBITORS

This is a division of application Ser. No. 07/452,138, filed Dec. 18, 1989, now U.S. Pat. No. 5,086,067.

BACKGROUND OF THE INVENTION

The present invention relates to pharmaceutical agents (compounds) which act as leukotriene $B_4$ ($LTB_4$) synthesis inhibitors in mammals. The compounds inhibit $LTB_4$ synthesis by inhibiting phospholipase $A_2$ ($PLA_2$) activity. $PLA_2$ is an important enzyme in the biosynthesis of leukotrienes as $PLA_2$ acts to release arachidonic acid from phospholipids. Once released, arachidonic acid is rapidly metabolized by a variety of enzymes of the arachidonic acid cascade to produce prostaglandins, leukotrienes and related compounds. The use of the compounds herein to inhibit $PLA_2$ activity thus inhibits the release of arachidonic acid from phospholipids. The inhibition of release of arachidonic acid similarly diminishes subsequent products in the arachidonic acid cascade, such as prostaglandins, leukotrienes, and related compounds, including $LTB_4$.

$LTB_4$ (Formula I) is an arachidonic acid metabolite which is produced by the 5-lipoxygenase pathway. Pharmacologically, $LTB_4$ is an important mediator of

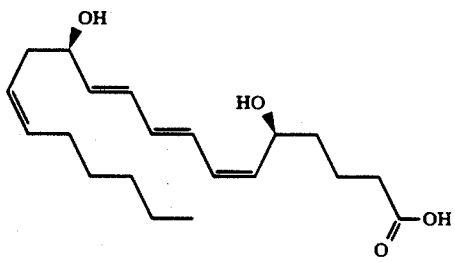

inflammation. $LTB_4$ is known to induce chemotaxis, chemokinesis, aggregation, and degranulation of leukocytes in vitro, and to induce accumulation of polymorphonuclear leukocytes, and increase vascular permeability and edema formation in vivo. Particularly high levels of $LTB_4$ are detected in lesions in inflammatory diseases such as rheumatoid or spondylarthritis, gout, psoriasis, ulcerative colitis, Crohn's disease, multiple sclerosis and some respiratory diseases. Since the compounds herein inhibit $PLA_2$ and thereby $LTB_4$, the compounds of the present invention are useful in treating inflammatory conditions in mammals such as psoriasis, Crohn's disease, ulcerative colitis, multiple sclerosis and the like.

Accordingly, it is an object of this invention to produce compounds for use as pharmaceutical agents which will exhibit $LTB_4$ inhibitory activity in mammals.

The pharmacology of the biologically active leukotrienes is generally discussed in J. Clin. Invest. 73, 889–897 (1984).

SUMMARY OF THE INVENTION

This invention relates to a compound of the formula:

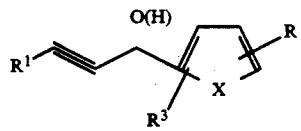

or a pharmaceutically acceptable salt thereof
wherein X is oxygen, sulfur, —CH=CH—, or CH=N;
wherein Y, when present, is hydrogen or halogen
wherein $R^1$ is alkyl, alkenyl, or alkynyl of about 1 to 20 carbon atoms;
wherein R is —$CO_2R^2$, tetrazole, methylsulfonamide or benzenesulfonamide;
wherein $R^2$ is hydrogen, alkyl of 1 to 6 carbons or a pharmaceutically acceptable cation; and wherein $R^3$ is hydroxyl or halogen.

This invention, more specifically, relates to a compound of the formula:

or a pharmaceutically acceptable salt thereof
wherein X is oxygen, sulfur, —CH=CH—, or CH=N;
wherein Y is hydrogen or halogen
wherein $R^1$ is alkyl, alkenyl, or alkynyl of about 1 to 20 carbon atoms;
wherein R is —$CO_2R^2$, tetrazole, methylsulfonamide, or benzenesulfonamide;
wherein $R^2$ is hydrogen, alkyl of 1 to 6 carbons or a pharmaceutically acceptable cation; and wherein $R^3$ is hydroxyl or halogen.

This invention also more specifically, relates to a compound of the formula:

or a pharmaceutically acceptable salt thereof
wherein X is oxygen, sulfur, —CH=CH—, or CH=N;
wherein Y is hydrogen or halogen
wherein $R^1$ is alkyl, alkenyl, or alkynyl of about 1 to 20 carbon atoms;
wherein R is —$CO_2R^2$, tetrazole, methylsulfonamide, or benzenesulfonamide;
wherein $R^2$ is hydrogen, alkyl of 1 to 6 carbons or a pharmaceutically acceptable cation; and wherein $R^3$ is hydroxyl or halogen.

DETAILED DESCRIPTION

This invention encompasses compounds of Formula VI as previously described. A particularly preferred embodiment of the present invention is encompassed by a compound of the formula:

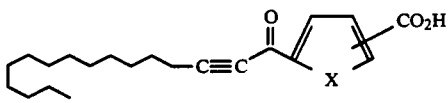

or a pharmaceutically acceptable salt thereof,
wherein X is oxygen, sulfur, —CH═CH—, or CH═N The term "lower alkyl" as used herein means straight or branched chain alkyls having 1–6 carbon atoms.

The term "pharmaceutically acceptable cation" as used to describe $R_2$ refers to cations such as ammonium, sodium, potassium, lithium, calcium, magnesium, ferrous, zinc, copper, manganous, aluminum, ferric, manganic, ammonium, tetraalkyl-ammonium, and the like.

The term "pharmaceutically acceptable non-toxic addition salts" refers either to those base derived salts of any compound herein having a carboxylic acid function.

The base derived salts can be derived from pharmaceutically acceptable non-toxic inorganic or organic bases. Among the inorganic bases employed to produce pharmaceutically acceptable salts are the hydroxide bases of the "pharmaceutically acceptable cations" disclosed above.

Among the organic bases employed to produce pharmaceutically acceptable salts are the pharmaceutically acceptable non-toxic bases of primary, secondary, and tertiary amines. Especially preferred non-toxic bases are isopropylamine, diethylamine, ethanolamine, dicyclohexylamine, choline, and caffeine.

All of the pharmaceutically acceptable non-toxic addition salts are prepared by conventional processes which are well known to those of ordinary skill in the art.

The compounds of this invention are generally prepared according to the reaction schemes I, II and III, wherein a side chain is substituted onto a halo aromatic acid or ester moiety. By halo is meant a halogen such as bromo, iodo, fluoro or chloro. In Scheme I, the halo group is represented by the term "halo." By aromatic moiety is meant phenyl, thienyl or furyl, corresponding to "X" in the aryl ring being —CH═CH—, —CH═N—, —S—, and —O—.

As disclosed in Scheme I, a side chain can be added to the aromatic moiety by performing a nucleophilic substitution of the halogen such as via a reaction with an alkyne, CO, and Pd[O].

Hydrogenation of the triple bond, such as by introducing hydrogen over palladium produces an enone containing side chain having the cis or trans configuration.

The reaction Scheme III illustrates another method for the addition of the side chain to the aromatic moiety. Substitution of the side chain onto the monohaloaromatic moiety to produce XV is accomplished by performing a nucleophilic substitution at the carbon bearing the halo group, preferably with a nucleophile, such as an alkyne, alkene, or a (tributylstannyl) alkyne in the presence of a catalyst, such as Pd[O], in a nonpolar solvent, such as toluene, and in the presence of heat.

The biological activity possessed by the compounds of this invention was indicated by positive results in assays for inhibition of human synovial fluid $PLA_2$ (HSF-$PLA_2$) and $LTB_4$ biosynthesis in HL-60 cells.

By virtue of their activity as $LTB_4$ synthesis inhibitors, the compounds of Formula I are useful in treating inflammatory conditions in mammals such as psoriasis, Crohn's disease, ulcerative colitis, multiple sclerosis and the like. Similarly, the compounds of Formula I can be used in preventing recurring inflammatory attacks. A physician or veterinarian of ordinary skill can readily determine whether a subject exhibits the inflammatory condition. The preferred utility relates to treatment of ulcerative colitis.

The compounds of the present invention can be administered in such oral dosage forms as tablets, capsules, softgels, pills, powders, granules, elixirs, or syrups.

The compounds can also be administered intravascularly, intraperitoneally, subcutaneously, intramuscularly, or topically using forms known to the pharmaceutical art. Moreover, they can be administered rectally or vaginally, in such forms as suppositories or bougies. In general, the preferred form of administration is oral. For the orally administered pharmaceutical compositions and methods of the present invention, the foregoing active ingredients will typically be administered in admixture with suitable pharmaceutical diluents, excipients, or carriers (collectively referred to herein as "carrier" materials) suitably selected with respect to the intended form of administration, that is, oral tablets, capsules, softgels, elixirs, syrups, drops, and the like, and consistent with conventional pharmaceutical practices.

For example, for oral administration in the form of tablets or capsules, a therapeutically effective amount of one or more compounds of the present invention can be combined with any oral non-toxic pharmaceutically acceptable inert carrier such as lactose, starch, sucrose, cellulose, magnesium stearate, dicalcium phosphate, calcium sulfate, mannitol, and the like, or various combinations thereof. For oral administration in liquid forms, such as in softgels, elixirs, syrups, drops and the like, a therapeutically effective amount of the active drug components can be combined with any oral non-toxic pharmaceutically acceptable inert carrier such as water, saline, ethanol, polyethylene glycol, propylene glycol, corn oil, cottonseed oil, peanut oil, sesame oil, benzyl alcohol, various buffers, and the like, or various combinations thereof. Moreover, when desired or necessary, suitable binders, lubricants, disintegrating agents, and coloring agents can also be incorporated in the mixture. Suitable binders include starch, gelatin, natural sugars, corn sweeteners, natural and synthetic gums such as acacia, sodium alginate, carboxymethylcellulose, polyethylene glycol, and waxes, or combinations thereof. Lubricants for use in these dosage forms include boric acid, sodium benzoate, sodium acetate, sodium chloride, and the like, or combinations thereof. Disintegrators include, without limitation, starch, methylcellulose, agar, bentonite, guar gum, and the like, or combinations thereof. Sweetening and flavoring agents and preservatives can also be included where appropriate.

For intravascular, intraperitoneal, subcutaneous, or intramuscular administration, one or more compounds of the present invention can be combined with a suitable carrier such as water, saline, aqueous dextrose, and the like. For topical administration, such as for psoriasis, therapeutically effective amounts of one or more compounds of the present invention can be combined with pharmaceutically acceptable creams, oils, waxes, gels and the like. Regardless of the route of administration selected, the compounds of the present invention are formulated into pharmaceutically acceptable dosage forms by conventional methods known to those skilled in the art. The compounds can also be formulated using pharmacologically acceptable base addition salts. Moreover, the compounds or their salts may be used in a suitable hydrated form.

Regardless of the route of administration selected, a non-toxic but therapeutically effective quantity of one or more compounds of this invention is employed in any treatment. The dosage regimen for preventing or treating inflammatory conditions with the compounds of this invention is selected in accordance with a variety of factors, including the type, age, weight, sex, and medical condition of the patient, the severity of the inflammatory condition, the route of administration, and the particular compound employed in the treatment. A physician or veterinarian of ordinary skill can readily determine and prescribe the effective amount of the drug required to prevent or arrest the progress of the condition. In so proceeding, the physician or veterinarian could employ relatively low doses a first and subsequently increase the dose until a maximum response is obtained. Daily dosages of the compounds of the invention are ordinarily in the range of about 1.0 mg/kg up to about 30.0 mg/kg, (preferably in the range of about 2.0 to 14.0 mg/kg (orally)).

The following examples illustrate the methods used to prepare the compounds of this invention. These examples are given by way of illustration only and are not meant to be construed as limiting the invention in spirit or in scope, as many modifications in materials and methods will be apparent from this disclosure to those skilled in the art.

In the following examples, and throughout this application, a wavy line ( ) defines a substituent as an asymmetric carbon having R or S stereochemistry or cis/trans isomers of a carbon-carbon double bond. In the structures herein a bond drawn across a bond in a ring indicates that the bond can be to any available carbon atom of the ring structure. A series of dashes for a bond used in the structures herein indicates that such a bond may or may not be present.

Scheme I

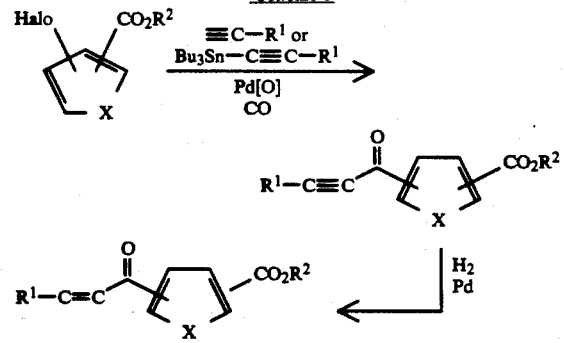

Scheme II

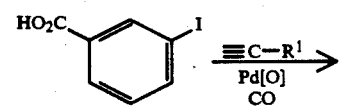

Scheme II (continued)

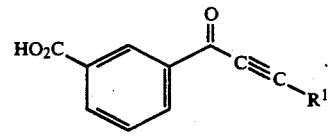

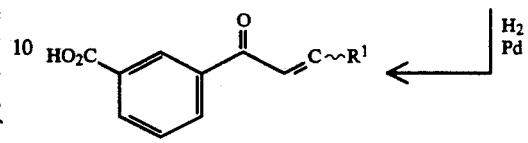

Scheme III

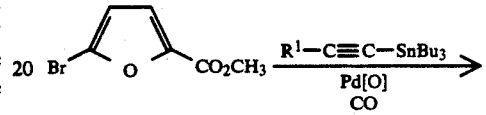

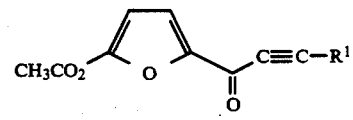

EXAMPLE 1

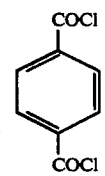

The above acid chloride was prepared from terphthalic acid by reacting 0.5 g (3 mmoles) of terphthalic acid with 2 cc of [COCl]$_2$ (23.6 mmoles) in 10 cc of benzene and with one drop of dimethylformamide. The reagents were mixed and warmed to 60° C. for twenty-four hours. The reaction mixture was cooled to room temperature and the volatile components were removed in vacuo to give the above compound as a pale yellow solid.

EXAMPLE 2

CH$_3$(CH$_2$)$_{11}$C≡C—TMS

The above compound was prepared by reacting an acetylene of the formula CH$_3$(CH$_2$)$_{11}$C≡CH (2.5 g, 12.87 mmoles) which was added to 25 cc of tetrahydrofuran (THF) and 50 mg of triphenylmethane (Ph$_3$CH) which was added as an indicator. The solution was cooled to −30° C. and 1.6 molar n-butyllithium (n-BuLi) was added dropwise until the solution turned red. Approximately 8.5 cc of n-BuLi was added. The solution was back titrated with the acetylene compound until it became colorless. The solution was cooled to −78° C. and 2 cc (15.75 mmoles) of trimethylsilyl chloride (TMS-Cl) was added. The solution was slowly warmed over a period of five hours to room temperature. The reaction was quenched with water and extracted with hexane. The hexane was washed once with water and once with brine and dried over magnesium sulfate (MgSO₄). The trimethylsilyl compound was isolated in an amount of 4.31 g (16.2 mmoles).

EXAMPLE 3

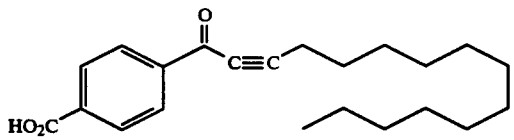

The above compound was prepared by reacting 3 mmoles of the acid chloride product from Example 1 with 0.8 g (3 mmoles) of the TMS-acetylene product from Example 2. The acid chloride and the TMS-acetylene product were dissolved in 10 cc of dichloromethane and cooled to 0° C. To the reaction mixture was added 0.8 g (6 mmoles) of aluminum chloride (AlCl₃) in small portions over ten minutes. The reaction mixture was stirred for about 1.5 hours at 0° C. The reaction was quenched with ice and the mixture was extracted three times with diethyl ether. The extracts were combined and washed once with water and once with brine (saturated sodium bicarbonate solution) and dried over magnesium sulfate to yield 0.29 g of the above product.

HRMS (M+): calculated 342.2195; found 342.2196

EXAMPLE 4

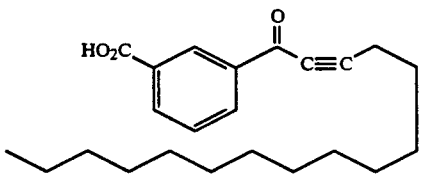

The above compound was prepared by mixing 3 g of m-iodobenzoic acid (12.1 mmoles) and 3.12 g (15.0 mmoles) of an acetylene derivative of the formula

with 0.085 g (0.121 mmoles) of a palladium catalyst, Pd(PPh₃)₂Cl₂ in 30 cc of Et₃N. The reaction vessel was purged with carbon monoxide. The reaction mixture was heated under a carbon monoxide atmosphere (atmospheric pressure, balloon) in an oil bath at 80° C. for two hours. The reaction mixture was cooled to room temperature. The volatile components were removed in vacuo and the residue was taken up in 5% hydrochloric acid and extracted with diethyl ether. The diethyl ether was washed once with 10% hydrochloric acid, twice with water, and once with a brine solution and dried over magnesium sulfate. The solvent was removed yielding 4.58 gm of the product. Chromatography on silica gel afforded 3.2 g of yellow solid which was triturated with cold hexane to give a tan solid of 2.97 g.

MP found: 77.5°–80.5° C.

Analysis calculated: C, 77.49; H, 9.05. Found: C, 77.22; H, 9.15.

EXAMPLE 5

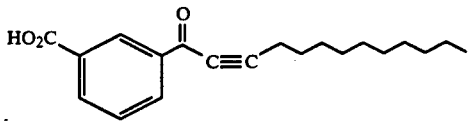

The above compound was prepared by mixing one gram (4.03 mmoles) of m-iodobenzoic acid and 0.83 g (5 mmoles) of an acetylene derivative of the formula

along with 0.028 g (0.04 mmoles) of the palladium catalyst used in Example 4. The reagents were mixed in 10 cc of triethylamine. The reaction vessel was purged with carbon monoxide. The reaction was performed under a carbon monoxide atmosphere (atmospheric pressure, balloon). The reaction mixture was heated in an oil bath at 80° C. for two hours. The reaction mixture was cooled to room temperature. The volatile components were removed in vacuo and the residue was taken up in 5% hydrochloric acid (HCl) and extracted once with diethyl ether. The diethyl ether extract was washed once with 10% HCl, twice with water and once with brine (NaCl) and dried over magnesium sulfate. The solvent was removed yielding a red yellow gum. After purification by silica gel chromatography 0.51 g of the product having the above structure was produced.

Analysis calculated: C, 76.40; H, 8.33. Found: C, 76.08; H, 8.42. MP Found: 69°–71° C.

EXAMPLE 6

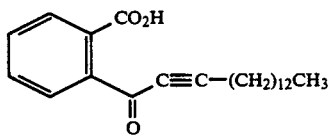

A solution of 1 g (4.8 mmoles) of an acetylene having the formula

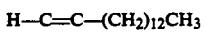

in 25 cc of THF which contained a trace (20 mgs) of triphenylmethane was treated with n-BuLi until the red color of the triphenylmethyl carbanion persisted. A few drops of the acetylene was added to discharge the red color. The reaction was performed at 0° C. The reaction mixture was stirred at 0° C. for 1¼ hours. The solution was added dropwise via syringe to a cooled (0° C.) solution of phthalic anhydride (3.7 g, 25 mmoles) in 50 ml of THF. The reaction mixture was stirred at room temperature for 2½ days. The reaction mixture was quenched with 10% aqueous HCl and extracted with ethyl acetate. The ethyl acetate extract was washed once with water, once with brine and dried over MgSO₄. After removal of the solvent, a gum was obtained. After purification by silica gel chromatography 0.104 g of the above product was recovered.

HRMS (M+): Calculated: 356.2352; Found: 356.2361.

EXAMPLE 7

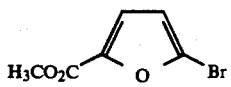

A solution of 10 g (52.4 mmoles) of a bromo-furanoic acid of the formula

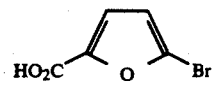

in 100 cc of methanol was prepared and cooled to 0° C. using an ice bath. 20 ml of concentrated sulfuric acid was added dropwise over 15 minutes. The ice bath was removed and the reaction mixture stirred for eighteen hours at room temperature overnight. The reaction mixture was poured onto 500 ml of water and extracted twice with diethyl ether. The extracts were combined and washed once with water, once with NaHCO$_3$, once again with water and brine and dried over magnesium sulfate. The solvent was removed to yield 6.77 g of a pale yellow solid.

EXAMPLE 8

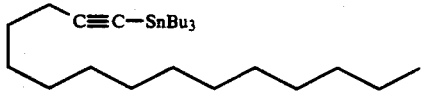

The above compound was prepared by reacting 2.02 g (9.7 mmoles) of the acetylene compound of the structure

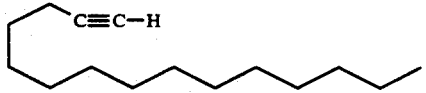

in 15 ml of THF at 0° C. To the solution was added 6.5 ml (10.4 mmoles) of 1.6 molar n-butyllithium. The reaction mixture was stirred for 25 minutes at 0° C. To the cooled milky solution was added 3 ml (11.1 mmoles) of ClSnBu$_3$ in a dropwise manner. The solution cleared to a pale yellow. The reaction was allowed to warm to room temperature. The reaction mixture was diluted with dichloromethane and washed with water and brine. The reaction mixture was dried over sodium sulfate, filtered and stripped to yield 5.13 g of the above product as a pale yellow oil.

EXAMPLE 9

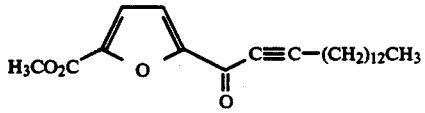

The above compound was prepared by reacting 0.21 g (1.01 mmoles) of the product from Example 7 and 0.5 g (1.01 mmoles) of the acetylene product from Example 8 in 5 cc of toluene. The palladium catalyst of Example 4, 7 mg (0.01 mmoles) was added to the reaction mixture. The reaction mixture was degassed and purged three times with carbon monoxide. The reaction mixture was heated 100° C. using an oil bath and stirred for eight hours at 100° C. The toluene solution was treated with saturated aqueous potassium fluoride solution for ½ hour. The mixture was then poured into diethyl ether and extracted twice with water and dried over magnesium sulfate. After filtration and removal of the solvent, a brown gummy solid was obtained. Following chromatography on silica gel the above product was obtained, 0.08 g (0.22 mmoles).

HRMS (M+) Found: 360.2303; Calculated: 360.2301.

EXAMPLE 10

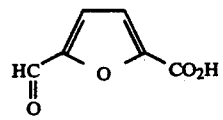

The above compound was prepared by forming a solution of 2.5 gms. (13.1 mmoles) of a bromo-furanoic acid in 25 ml of tetrahydrofuran (THF) which was cooled to −78° C. To the solution was added a 1.6 molar solution of n-butyl lithium in hexane (17.5 ml, 28 mmoles) which was stirred at −78° for one hour. Dimethylformaide (DMF) was added in an amount of 2.4 ml (30 mmoles). The solution was allowed to warm to room temperature. The reaction mixture was quenched with water and acidified with 10% hydrochloric acid. The resultant reaction mixture was extracted twice with ethyl acetate, the combined extracts were washed twice with water and once with brine and subsequently dried over magnesium sulfate. An orange solid was obtained after removal of the solvent in vacuo. Following chromatography on silica gel 0.73 gms. of the compound of the above formula was obtained.

EXAMPLE 11

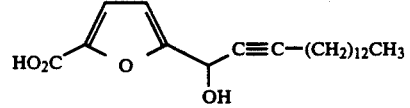

The above compound was prepared by forming a solution of 1.2 gms. (6 mmoles) of an acetylene of the formula H≡(CH$_2$)$_{12}$CH$_3$ in 25 ml. THF which contained a catalytic amount (20 mg.) of triphenylmethane. The solution was cooled to −50° C. and then treated with 3.75 ml. (6 mmoles) of n-BuLi until the red color of the triphenylmethane anion persisted. A few drops of the acetylene compound was added until the color disappeared. An amount of 0.42 gms. of the product formed in Example 10 in 10 ml. THF was added drop-wise to the solution. The mixture was warmed to 0° C. over one-half hour. The mixture was quenched with water and acidified with 10% hydrochloric acid. The aqueous phase was extracted twice with ethyl acetate. The extracts were combined and washed twice with water and once with brine and were dried over magnesium sulfate. Chromatography on silica gel yielded 0.80 gms. of a pale yellow solid.

HRMS (M+) Calculated: 348.2301; Found: 348.2291.

EXAMPLE 12

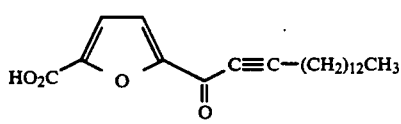

The compound was prepared by reacting 0.145 g. (4.2 mmoles) of the product from example 11 in acetone (25 ml) and adding 1.5 g. of activated MnO₂ portionwise over five minutes. The reaction mixture was stirred for 24 hours at room temperature. The reaction mixture was poured into 10% hydrochloric acid and extracted with ethyl acetate. The extract was washed once with water and dried over magnesium sulfate. After the solvent was removed in vacuo a white solid remained. Following chromatography on silica gel, 60 mg. of a white solid was recovered.

Analysis (for hydrate with 0.35 H₂O); Calculated: C, 71.50; H, 8.77; Found: C, 71.55; H, 8.63.

EXAMPLE 13

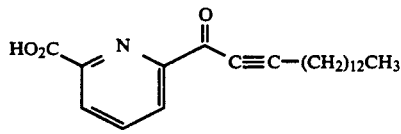

The above compound was prepared by forming a solution of 0.83 gms. (4 mmoles) of an acetylene of the formula H—C≡C—(CH₂)₁₂CH₃ in 25 ml. THF containing a catalytic amount (20 mgs.) of triphenyl methane. The solution was cooled to −50° C., then treated with 2.5 ml. of a 1.6 molar solution (4 mmoles) of n-BuLi in hexane until the red color of the triphenylmethane anion persisted. A few drops of the acetylene was added until the color disappeared. The resultant lithium acetylide preparation was cooled to −78° C. A solution (6 mmoles) of a diacid chloride of the formula

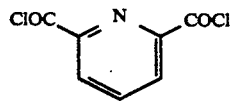

was cooled to −78° C. and the −78° C. solution of lithium acetylide was added dropwise via a cannula. The reaction was stirred for 10 minutes and quenched with water and warmed to room temperature. The reaction mixture was poured into water and acidified with acetic acid (HOAc). The aqueous solution was extracted twice with ethyl acetate and the extracts were washed twice with water, once with brine and dried over magnesium sulfate. Following chromatography on silica gel 0.95 gms. of a product of the above formula was recovered.

Analysis calculated: C, 73.92; H, 8.74; N, 3.92; Found: C, 73.64; H, 8.79; N, 3.86.

EXAMPLE 14

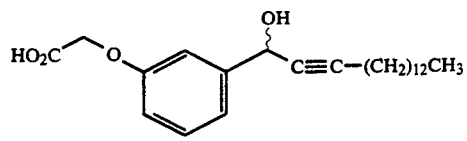

The compound of the above formula was prepared in the following manner. An acetylene solution was prepared by dissolving 0.83 gms. (4 mmoles) of an acetylene of the formula H—C≡C—(CH₂)₁₂CH₃ in 25 ml. of THF and 20 mgs. of triphenylmethane. The solution was cooled to −50° C. and treated with n-BuLi until the red color of the triphenylmethane anion persisted. A few drops of the acetylene was added until the color disappeared. An aldehyde of the following formula

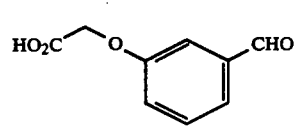

in an amount of 0.36 gms. (2 mmoles) was added dropwise to the solution and the mixture was warmed to 0° C. The reaction mixture was quenched with water and acidified with 10% hydrochloric acid. The aqueous phase was extracted twice with ethyl acetate and the extracts were washed twice with water, once with brine and dried over magnesium sulfate. Upon chromatography over silica gel 0.55 gms. (1.42 mmoles) of a product of the above formula was recovered.

Analysis calculated: C, 74.19; H, 9.34; Found: C, 74.21; H, 9.47.

EXAMPLE 15

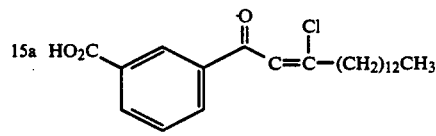

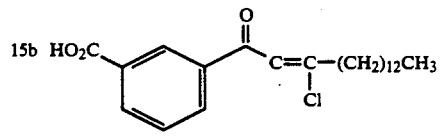

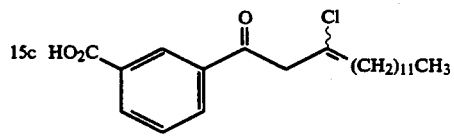

The above three compounds were prepared in the following manner. An acid chloride of the structure

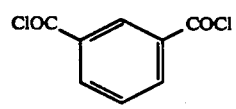

was prepared in a manner as recited in Example 1 in an amount of 15.05 mmoles was dissolved in 50 ml. of dichloromethane and cooled to 0° C. To the solution was added 3.2 gms. (15 mmoles) of an acetylene of the formula H—C≡C—(CH$_2$)$_{12}$CH$_3$. 2 gms. of aluminum chloride was added portionwise over one-half hour and the reaction mixture was stirred at 0° C. for one hour. The reaction mixture was quenched with ice, diluted with ether and washed twice with water and dried over magnesium sulfate. Following separation by chromatography on silica gel 42 mg. and 30 mg of the isomers of the above formulae 15a and 15b were obtained and 23 mg. of the isomer of the above formula 15c was obtained.

For 15a HRMS (M+) Calculated: 392.2118; Found: 392.2122.

For 15b HRMS (M+) Calculated: 392.2118; Found: 392.2121.

For 15c HRMS (M+) Calculated: 392.2118; Found: 392.2113.

EXAMPLE 16

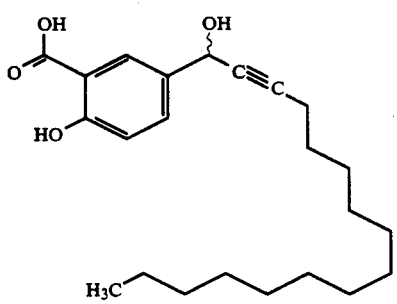

A compound of the above structure was prepared by forming a solution of an acetylene of the formula H—C≡C—(CH$_2$)$_{12}$CH$_3$ in 25 ml. of THF and 20 mgs. of triphenylmethane. The solution was cooled to −50° C. and treated with n-BuLi until the red color of the triphenylmethane anion persisted. A few drops of acetylene was added until the color disappeared. An aldehyde of the formula

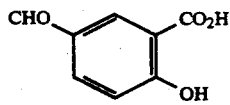

in an amount of 0.33 gms. (2 mmoles) in 5 ml. of THF was added dropwise to the solution and the mixture was warmed to 0° C. The reaction mixture was quenched with water and acidified with 10% hydrochloric acid. The aqueous phase was extracted twice with ethyl acetate and the extracts were washed twice with water, once with brine and dried over magnesium sulfate. Upon separation by chromatography on silica gel, 0.447 gms. (1.2 mmoles) of the product of the above formula was recovered as a white solid.

Analysis calculated: C, 73.76; H, 9.15; Found: C, 73.54; H, 9.26.

EXAMPLE 17

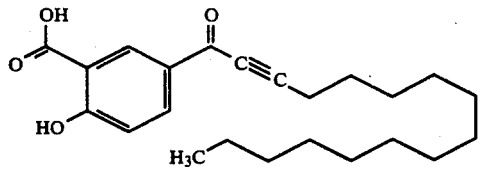

The compound of the above formula was prepared in the following manner. 0.1 gms. (0.27 mmoles) of the compound prepared in Example 16 was dissolved in 10 cc. of acetone. Activated manganese dioxide (1 gm.) was added portionwise. The reaction mixture was stirred for 24 hours. The crude reaction mixture was filtered through celite and the solvent evaporated. Following chromatography over silica gel 0.55 gms. of a product of the above formula was produced as a white solid.

HRMS (M+) Calculated: 372.2300; Found: 372.2291.

EXAMPLE 18

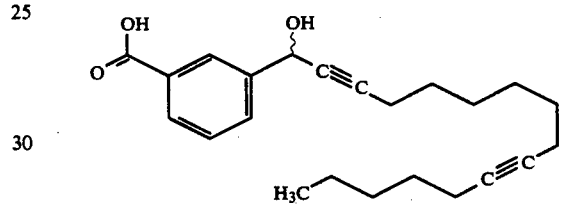

The above compound was prepared in the following manner. Decadiyne in the amount of 6.71 gms. (15 mmoles) was dissolved in 200 ml. of THF, along with 50 mgs. of triphenylmethane. The mixture was cooled to −50° C. and 31.3 ml. (50 mmoles) of 1.6 molar n-BuLi in hexane was added until the red color of the triphenylmethane anion persisted. Additional decadiyne was added until the red color disappeared. The reaction mixture was warmed to −20° C. and stirred for one-half hour. The reaction mixture was cooled to −40° C. and 9.9 gms. (50 mmoles) of iodohexane was added dropwise. Following the addition of the iodohexane, 50 ml. of HMPA was added dropwise and the reaction mixture was stirred and allowed to warm to room temperature. The reaction mixture was quenched with water and poured into hexane and washed with four washings of water, one with brine and dried over magnesium sulfate. The crude product contained the diyne of the formula H—C≡C—(CH$_2$)$_6$—C≡C—C$_5$H$_{11}$.

A lithium acetylide was prepared by treating the crude diyne with 14.7 mmoles of n-BuLi at −20° C. until the color of the triphenylmethane anion was present. Triphenylmethane (25 mgs) was added. An excess of the acetylene was added until the color disappeared. The reaction mixture was cooled to −50° C. and 1 gm. (6.7 mmoles) of an aldehydic acid of the formula

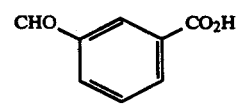

in 10 mls. of THF was added dropwise. The reaction mixture was warmed to room temperature over 1 hour and the reaction was quenched with water. The bulk of THF was removed in vacuo and the residue partitioned between diethyl ether and water. The diethyl ether layer was dried over magnesium sulfate. Upon chromatography 1.11 gms. (3.13 mmoles) of the product of the above formula was produced as a yellow oil which solidified on standing.

Analysis calculated: C, 77.93; H, 8.53; Found: C, 78.02; H, 8.43.

HRMS (M+) Calculated: 354.2195; Found: 354.2195.

EXAMPLE 19

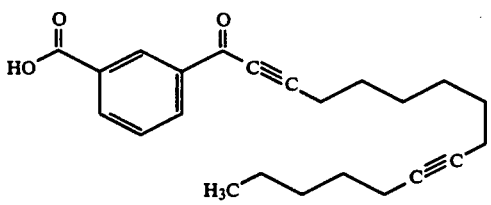

The compound of the above formula was prepared in the following manner. A solution was prepared by dissolving 0.125 gms. (0.35 mmoles) of the product from Example 18 in 15 ml. of acetone. To the solution was added 1 gm. of manganese dioxide ($MnO_2$). The manganese dioxide was added portionwise over a period of 15 minutes. The reaction mixture was stirred for 24 hours at room temperature. The reaction mixture was poured into 10% hydrochloric acid and extracted with ethyl acetate. The extract was washed once with water and dried over magnesium sulfate. The solvent was removed in vacuo and the product was isolated using chromatography on silica gel to provide 0.90 gms. of a product of the above formula.

Analysis calculated: C, 78.38; H, 8.01; Found: C, 78.53; H, 8.18.

EXAMPLE 20

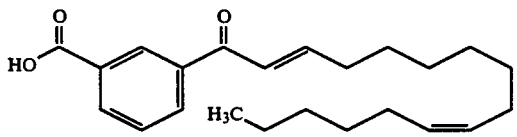

A compound of the above formula was prepared in the following manner. 10 mgs. (0.028 mmoles) of the compound prepared in Example 19 was mixed with 2.0 ml. of hexane and 1 mg. of a Lindlar catalyst and 0.01 ml. of a quinoline. The reagents were mixed and the reaction vessel was degassed 3 times with hydrogen delivered from a balloon. The reaction mixture was monitored closely via TLC and stirred at room temperature. The reaction vessel was evacuated and purged three times with argon. The reaction mixture was then filtered through celite. The filtrate was washed once with 10% hydrochloric acid, once with water, once with saturated sodium bicarbonate, once with saturated sodium chloride, and dried over magnesium sulfate. Following separation by chromatography 0.008 gms. of a product of the above formula was recovered as a mixture of E and Z isomers about the enone double bond.

HRMS (MH+) Calculated: 357.2430; Found: 357.2432.

EXAMPLE 21

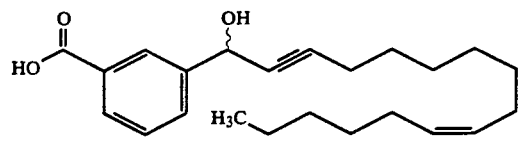

A compound of the above structure was prepared in the following manner. To a solution of 0.1 gms. of the product from Example 18 (0.282 mmoles) in 1 ml. of DMF was added 0.1 gms. (1.5 mmoles) of imidazole, followed by 0.19 gms. (0.7 mmoles) of t-butyldiphenylsilyl chloride (TBDPS-Cl) at room temperature under argon. The solution was stirred for 4 hours at room temperature. The reaction mixture was diluted with 200 ml. of diethyl ether and washed 3 times with water (30 ml. each), once with brine and dried over magnesium sulfate. Removal of the solvent yielded an oil which upon separation by chromatography on silica gel yielded 0.11 gms. of a product of the formula

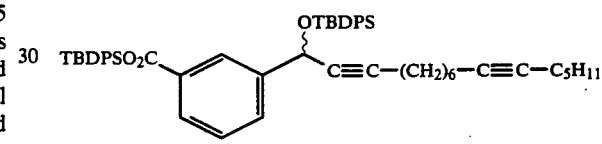

This product, 0.11 g (0.13 mmoles) was mixed with 10 ml. of hexane, 5 mgs. of a Lindlar catalyst and 0.05 ml of quinoline. The reaction mixture was stirred at room temperature under hydrogen and after 1 hour TLC indicated the reaction was complete. The reaction vessel was evacuated and purged 3 times with argon. The reaction mixture was filtered through celite, diluted with hexane and washed once with 5% hydrochloric acid, once with water, once with brine and dried over magnesium sulfate. The resultant product produced was 0.11 gms of a product of the formula

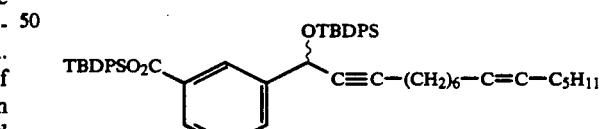

A solution of this product was prepared by dissolving 0.11 gms. in 10 ml. of THF, which was then treated with 1.5 ml. of 1 molar n-Bu$_4$NF in THF. After the starting material was consumed (via TLC), the reaction mixture was diluted with diethyl ether and washed with water and dried over magnesium sulfate. Following chromatography 0.037 gms. (0.103 mmoles) of the above identified product was recovered.

HRMS (MH+) Calculated: 357.2430; Found: 357.2444.

EXAMPLE 22

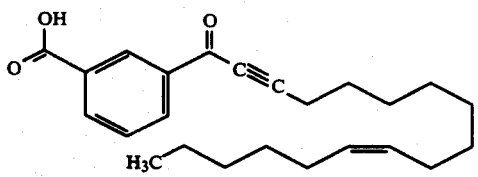

A compound of the above formula was prepared in the following manner. The compound prepared in Example 21, 0.030 gms., was dissolved in 3 ml. of acetone and 0.3 gms. of MnO$_2$ was added portionwise over 5 minutes. The reaction mixture was stirred for 24 hours at room temperature. The reaction mixture was then poured into 10% hydrochloric acid and extracted with ethyl acetate. The extract was washed once with water and dried over magnesium sulfate. After the solvent was removed in vacuo the resultant product was separated by chromatography over silica gel, yielding 0.021 gms. of product of the above formula.

HRMS (M+) Calculated 354.2192; Found 354.2195.

EXAMPLE 23

A compound of the above formula was prepared in the following manner. To a cooled (0° C.) solution of 5.5 ml. (39.2 mmoles) of diisopropylamine in 50 ml. of THF was added 20.5 ml. of 1.6 molar BuLi (32.8 mmoles) to make 32.8 mmoles of lithium diisopropylamide (LDA). The reaction mixture was stirred for one-half hour at 0° C. and cooled to −78° C. To the mixture was added 2.1 gm (16.4 mmoles) of 2-thiophene carboxylic acid in 25 ml. THF. Additional THF was added to increase the volume to 200 ml. and the reaction mixture was stirred for one-half hour. DMF was added in an amount of 1.3 ml. (16.8 mmoles). The reaction mixture was warmed to room temperature and stirred for 1½ hours. The reaction mixture was quenched with water and acidified with 1N hydrochloric acid and extracted with ethyl acetate. The organic extracts were combined and dried over magnesium sulfate. The resultant mixture was filtered and stripped to yield a yellow solid. Separation using chromatography on silica eluting with ethyl acetate/hexane/1% acetic acid provided 1.3 gms. of a yellow solid of the above formula. MP 160°-163°.

Analysis calculated: C, 46.15; H, 2.58; Found: C, 46.11; H, 2.82.

EXAMPLE 24

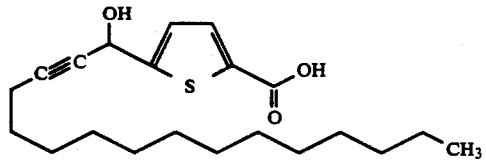

The compound with the above structure was prepared in the following manner. An acetylene of the formula H—C≡C—(CH$_2$)$_{12}$CH$_3$ in an amount of 549.3 mg. (2.6 mmoles) in 15 ml. of THF was cooled to −20°. To the solution was added 1.6 ml. (2.6 mmoles) of n-BuLi. The reaction was stirred for one half hour and 203.4 mg. (1.3 mmoles) of the product from Example 23 in 10 ml. of THF was added. The mixture was stirred and maintained at −20° for 15 minutes and allowed to warm to 0° C. and stirred for one-half hour. The reaction mixture was quenched with water and acidified with 10% hydrochloric acid and extracted with ethyl acetate. The combined organic extracts were dried over magnesium sulfate. The extract was filtered and stripped to yield a yellow oil which solidified upon standing. The solid was dissolved in ethyl acetate and filtered through silica gel eluting with 100% hexane followed by ethyl acetate in 1% acetic acid. The ethyl acetate fraction yielded 392.8 mg. of the above compound as a yellow solid having a melting point of 75°-90°.

Analysis calculated: C, 69.19; H, 8.85; Found: C, 69.18; H, 9.02.

EXAMPLE 25

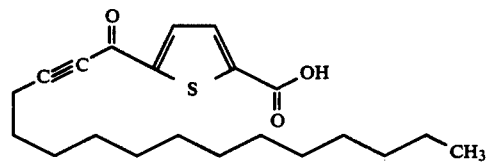

A compound of the above structure was formed in the following manner. 7.2 mg. (0.020 mmoles) of the compound prepared in Example 24 was dissolved in 1 ml. acetone. To the solution was added 72 mg. (0.83 mmoles) of activated manganese dioxide. The reaction mixture was stirred vigorously at room temperature overnight. The reaction mixture was poured into 10% hydrochloric acid. The aqueous phase was extracted with ethyl acetate. The organic washes were combined and dried over magnesium sulfate. The organic phase was filtered and stripped to yield 6 mg. (0.010 mmoles) of the above product as a white solid.

HRMS (M+) Calculated: 362.1916; Found: 362.1910.

EXAMPLE 26

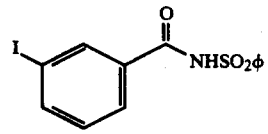

A compound of the above formula was prepared in the following manner. m-Iodobenzoic acid was reacted in an amount of 569 mgs. (2.29 mmoles) with 440 mg. (2.30 mmoles) of 1-(3-dimethylaminopropyl)-3-ethyl carbodiimide.HCl in 25 ml. of DMF. To the reaction mixture was added 0.35 ml. (2.51 mmoles) of Et$_3$N and 361 mg. (2.30 mmoles) of NH$_2$SO$_2$(C$_6$H$_5$). The reaction mixture was stirred at room temperature for 12 hours. The reaction mixture was poured into water and extracted with ethyl acetate. The organic extracts were combined and washed with brine and dried over magnesium sulfate. Following chromatography on silica gel eluting with ethyl acetate/hexane/1% acetic acid, 126 mg. of a white solid of the product with the above formula was recovered.

EXAMPLE 27

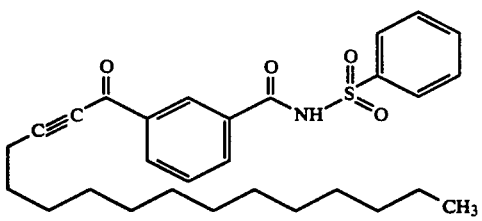

A compound with the above formula was prepared in the following manner. The compound from Example 26 in an amount of 77 mg. (0.20 mmoles) was combined with 49 mg. (0.24 mmoles) of an acetylene of the formula H—C≡C—$(CH_2)_{12}CH_3$ and 3 mg. (0.004 mmoles) of $Pd(Ph_3)_2Cl_2$ in 2 ml. of $Et_3N$. The mixture was heated in an oil bath at about 80° C. The reaction vessel was purged 4 times with carbon monoxide from a carbon monoxide balloon and permitted to react with stirring under carbon monoxide for 2.5 hours. The reaction mixture was then stirred at room temperature for about 60 hours. The solvent was evaporated under nitrogen. The residue was dissolved in ethyl acetate and washed with successive washes of 10% hydrochloric acid, water and brine. The organic layer was dried over magnesium sulfate, filtered and stripped to yield a brown oil. Upon chromatography on silica gel, 35 mgs. of a compound with the above formula was recovered as a brown oil.

HRMS ($MNH_4^+$) Calculated: 513.2787; Found: 513.2761.

EXAMPLE 28

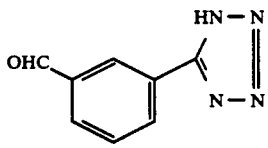

A compound having the above formula was prepared in the following manner. A solution of m-cyanobenzaldehyde was prepared by dissolving 2.0 gms. (15.2 mmoles) of the benzaldehyde along with 2.98 gms. (45.8 mmoles) of $NaN_3$ and 2.9 gms. (21.1 mmoles) of $Et_3N.HCl$, all of which were dissolved in 50 ml. of 1-methyl-2-pyrrolidinone. The reaction mixture was refluxed under argon. After 1 hour and 45 minutes the reaction mixture was cooled to room temperature and poured into 200 ml. of water and acidified with 10% hydrochloric acid. The reaction mixture was extracted with successive ethyl acetate washes. The ethyl acetate extracts were combined and washed with brine and dried over magnesium sulfate. The ethyl acetate extract was chromatographed through silica gel, yielding 0.3 gms. of the product having the above formula as a white solid.

EXAMPLE 29

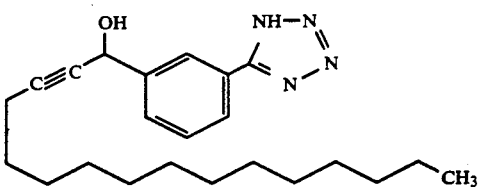

A compound of the above formula was prepared in the following manner. A solution of 5.03 g (24.1 mmoles) of an acetylene of the formula HC≡$C(CH_2)_{12}CH_3$ was dissolved in 100 ml. THF and cooled to −30° C. To the solution was added 15 ml. (24 mmoles) of a 1.6 molar n-BuLi solution which was added dropwise. The reaction mixture was stirred for 15 minutes at which time 2.1 gms. (12.0 mmoles) of the product from Example 28 dissolved in 75 ml. of THF was added dropwise. The solution was stirred and maintained at −30° C. for one-half hour, then warmed to room temperature. The reaction mixture was quenched with water and acidified with 10% hydrochloric acid. The layers were separated and the organic phase was washed with brine and dried over sodium sulfate. The layer was filtered and stripped to yield a yellow solid which upon chromatography over silica gel yielded 3.75 gms. of the above product as a white solid.

Analysis calculated: C, 72.21; H, 8.96; N, 14.65; Found: C, 72.03; H, 9.00; N, 14.77.

EXAMPLE 30

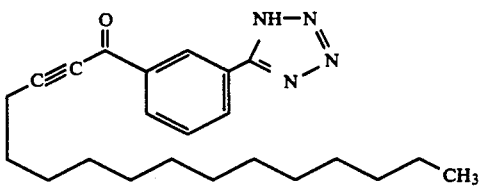

The compound having the above formula was prepared in the following manner. A solution was prepared by dissolving 36.2 mgs. (0.095 mmoles) of the product from Example 29 in acetone. To the solution was added 360 mgs. (4.14 mmoles) of activated manganese dioxide. The reaction mixture was stirred vigorously at room temperature overnight. The reaction mixture was poured into 10% hydrochloric acid. The aqueous phase was extracted with ethyl acetate and the organic washes were combined and dried over magnesium sulfate. The organic phase was filtered and stripped to yield 18 mgs. of a pale yellow solid of a compound having the above formula.

Analysis calculated: C, 72.59; H, 8.48; N, 14.72; Found: C, 72.19; H, 8.66; N, 14.13.

ASSAY FOR $LTB_4$ AND $PGE_2$ PRODUCTION BY HL-60 CELLS

HL-60 cells were induced to differentiate into granulocytes by a 4 day incubation with 0.8% (v/v) N,N-dimethyl formamide as disclosed in Fontana et al., Proc. Natl. Acad. Sci. 78 (6):3863-3866 (1981); Agins et al., Biochem. Biophys. Res. Comm. 126, 143-149 (1985); and Bonser et al., Biochemistry 20: 5297-5301 (1981). Prior to performing the assay, differentiated HL-60 cells were washed once with Hanks' balanced salt solution containing 0.35 mg/ml sodium bicarbonate and 10 mM HEPES pH 7.35 (HBSS). HL-60 cells ($3 \times 10^6$ cells/ml) were pre-incubated with the compound tested or a control vehicle at 37° C. for 10 minutes, followed by 5 minute incubation with $5 \times 10^{-6}$M calcium ionophore A23187 in a final volume of 1.0 ml. After incubation, the cells were pelleted by centrifugation and the $LTB_4$ and $PGE_2$ in the supernatent were quantified by radioimmunoassay. $IC_{50}$ values (means +/−S.E.) for compounds herein that were tested are shown in the following Table and represent the concentrations of the compound required to inhibit 50% of $LTB_4$ or $PGE_2$ production by HL-60 cells stimulated with the calcium ionophore A23187.

HUMAN SYNOVIAL FLUID PHOSPHOLIPASE $A_2$ (HSF-PLA$_2$) ASSAY

Human synovial fluid phospholipase $A_2$ was purified approximately 5000 fold following the procedures of Franson et al., Lung 160, 275-284 (1982) and Fawzy et al., Bio Phys. J. 49, 533a (1986). Following purification the enzyme activity was measured by established methodology using [$^{14}$C]-oleate-labeled, autoclaved E. coli as the substrate as also shown in the above noted references. The assay was performed in a final volume of 100 ml containing 50 mM HEPES (pH 7.0), 150 mM NaCl, 5 mM CaCl$_2$, 7 mM [$^{14}$C]-oleate-labeled E. coli phospholipid and with or without the compound from one of the examples herein undergoing an assay. The compound or control vehicle was pre-incubated with the PLA$_2$ for 5 minutes followed by addition of the E. coli substrate to initiate the reaction. The reaction was maintained at 37° C. for 30 minutes and then terminated by the addition of 2 ml tetrahydrofuran (THF). The reaction product, [$^{14}$C]-oleic acid, was extracted using a 1 ml Bond Elut-NH$_2$ Solid phase extraction column. The $IC_{50}$ value for the compound (mean +/−S.E.) is given in the following Table and represents the concentration of the compound required to inhibit 50% of the PLA$_2$ activity.

TABLE

| Example # | HSF-PLA2 IC50 uM | LTB4 Biosynthesis inhibition (HL60 cells) IC50 uM |
|---|---|---|
| 3 | 14 | 0.2 |
| 4 | 11 | 0.8 |
| 6 | 13 | — |
| 11 | 28 | 2.4 |
| 12 | 34 | 0.5 |
| 13 | 2.5 | 0.8 |
| 16 | 11 | 8 |
| 17 | 33 | 0.4 |
| 18 | 28 | — |

TABLE-continued

| Example # | HSF-PLA2 IC50 uM | LTB4 Biosynthesis inhibition (HL60 cells) IC50 uM |
|---|---|---|
| 24 | 18 | 0.9 |
| 25 | 15 | 0.4 |
| 27 | 14 | — |
| 29 | 42 | — |
| 30 | 11 | 0.9 |

What is claimed is:

1. A compound of the formula:

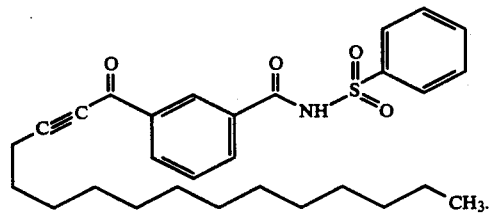

2. A compound of the formula:

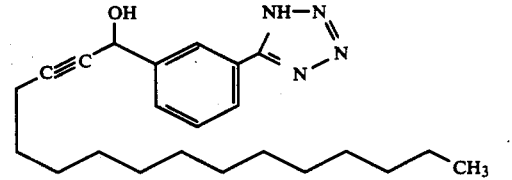

3. A compound of the formula:

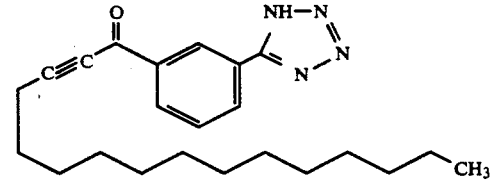

4. A pharmaceutical composition comprising a therapeutically or prophylactically effective amount of a compound according to claim 1 in a pharmaceutically acceptable carrier.

5. A pharmaceutical composition according to claim 4 wherein said composition is in oral dosage form.

6. A pharmaceutical composition comprising a therapeutically or prophylactically effective amount of a compound according to claim 2 in a pharmaceutically acceptable carrier.

7. A pharmaceutical composition comprising a therapeutically or prophylactically effective amount of a compound according to claim 3 in a pharmaceutically acceptable carrier.

* * * * *